United States Patent [19]

Ukai et al.

[11] 4,078,147

[45] Mar. 7, 1978

[54] HYDROXY ACID ESTERS OF HIGHER ALCOHOLS

[75] Inventors: Akitoshi Ukai; Yutaka Usui, both of Yokohama, Japan

[73] Assignee: The Nisshin Oil Mills, Ltd., Tokyo, Japan

[21] Appl. No.: 612,143

[22] Filed: Sep. 10, 1975

[51] Int. Cl.$^2$ .............................................. C07C 69/66
[52] U.S. Cl. .................................. 560/180; 252/121; 424/64; 424/70; 424/71
[58] Field of Search ................ 260/484 P; 424/64, 71, 424/70; 252/121

[56] References Cited

U.S. PATENT DOCUMENTS

| 1,993,736 | 3/1935 | Graves | 260/484 P |
| 1,993,737 | 3/1935 | Graves | 260/484 P |
| 2,122,716 | 7/1938 | Graves | 260/484 P |

*Primary Examiner*—Paul J. Killos
*Attorney, Agent, or Firm*—Sughrue, Rothwell, Mion, Zinn and Macpeak

[57] ABSTRACT

Hydroxy diester compounds are obtained by esterification between malic acid or tartaric acid and a saturated, aliphatic alcohol of 16 or more carbon atoms having side chains. These compounds are a colorless, odorless synthetic oil with low cloud point, which have a wide range of from low viscosity to high viscosity depending on the starting materials. Said synthetic oils are useful for basic oils or emulsions in the fields of cosmetics, detergents and medicinal preparations.

20 Claims, No Drawings

HYDROXY ACID ESTERS OF HIGHER ALCOHOLS

BACKGROUND OF THE INVENTION

This invention relates to a new synthetic oil and particularly, to a synthetic oil useful as basic oils (or emollient materials) and emulsions for cosmetics, detergents and medicinal preparations and a process for producing same.

Various natural fat and oil have been applied for the above uses, but are not necessarily satisfactory. Namely, the natural fat and oil have disadvantages that they undergo a large change in qualities and costs as agricultural products, it is difficult to obtain a colorless, odorless and tasteless products even with use of a high level of refining technique, and an offensive smell occurs with the lapse of time because of the double bond being present in the molecule.

Further, most of the natural fat and oil have a low viscosity of about 0.6 poises at 25° C and there is only castor oil (about 6 poises, 25° C) as the natural oil having relatively high viscosity. The natural fat and oil are, therefore, limited in the viscosity range. Accordingly, the natural fat and oil are unsuitable for use in basic oils or emulsions where a high viscosity is required.

Also, the natural fat and oil are, in general, not very low in a cloud point, i.e. mostly higher than −20° C, and therefore, this also results in limiting the uses.

Furthermore, in case basic oils are used in cosmetics and medicinal preparations such as ointments and emulsions, the following properties are required:

(1) less irritant effect on the skin, (2) colorless, odorless and tasteless, (3) non-coloring or non-rancid with the lapse of time, (4) good feeling in the skin, i.e. suitable spread, non-stickiness and good affinity, (5) low cloud point, (6) good miscibility with other ingredients, and (7) having a proper viscosity in accordance with the use. For such basic oils, olive oil, almond oil, castor oil and the like have been used, but they have the disadvantages as mentioned above.

Polyalkylene glycol and its derivatives are used as the basic oil having high viscosity, but they are quite different in the chemical structure from the sebum of the human body and therefore, not necessarily suitable for use in the cosmetics and ointments.

SUMMARY OF THE INVENTION

An object of this invention is to provide colorless, odorless and tasteless, synthetic oils with low cloud point, which have a wide range of from a low viscosity to a high viscosity and exhibit little degradation with the lapse of time.

Other object of this invention is to provide basic oils or emulsions having a wide range of from a low viscosity to a high viscosity, which meet the above-mentioned properties required for use in cosmetics and medicinal preparations.

The synthetic oil of this invention is a new compound which has not been reported in the literatures, and may be represented by the Formula,

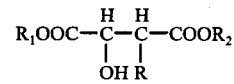
    I wherein R is hydrogen or hydroxyl, $R_1$ and $R_2$ which may be the same or different are an alkyl group of 16 or more carbon atoms having a side chain.

The basic oils or emulsions of this invention include at least one of mono- and di-hydroxy diester compounds of the Formula I as the effective ingredient.

We have also found that the oxyacid esters of the Formula I have satisfactory properties for the basic oils or emulsions in cosmetics, medicinal preparations, soaps, rinse and the like.

DETAILED DESCRIPTION OF THE INVENTION

The oxyacid esters of the Formula I may be obtained by effecting esterification between an oxyacid of the Formula II,

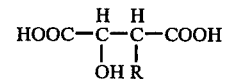
    II wherein R is as defined above and at least one of a saturated alcohol having a side chain, represented by the Formula III,

—OH    III wherein $R_3$ is an alkyl group of 16 or more carbon atoms having a side chain, in accordance with per se known methods.

The side chain containing alcohols of the Formula III which may be used as the starting material are known or may by synthesized in accordance with known methods, for example, Guerbet reaction and aldol condensation or in a method analogous to the processes described herein or to known methods.

The side chain containing alkyl group as mentioned above should have 16 or more carbon atoms. If the number of carbon atoms is less than 16, the obtained product is undesirable because of exhibiting irritant effect on the skin and having odor. The alkyl group may contain one or two or more side chains which may be a straight or branched carbon chain. Preferably, the side chain is in the β-position. Typical examples of the alcohols of the Formula III include 2-hexyl decanol, 2-octyl dodecanol, 2-heptyl undecanol and 5,7,7-trimethyl-2-(1,3,3-trimethylbutyl)-octanol-1. The starting alcohols may be used alone or in mixture for the esterification reaction.

The esterification may be effected in accordance with known methods, for example, a method using acid halides, an ester interchange and an esterification in the presence of or in the absence of catalysts under normal or reduced pressure. The method using acid halides, for example, comprises reacting an oxyacid with thionyl chloride and then reacting the resulting acid chloride with alcohols. Examples of the catalyst to be used include acids such as sulfuric acid, hydrochloric acid and para-toluenesulfonic acid, metal chlorides such as zinc chloride and stannous chloride, metals such as nickel and zinc, and metal oxides such as zinc oxide and magnesium oxide.

The reaction temperature is comprised between 100° C and 160° C, preferably 100° C and 140° C. In case the temperature is lower than 120° C, it is desirable from the point of reaction velocity to effect the reaction under reduced pressure.

The synthetic oils of this invention which undergo no change in qualities and costs as opposed to the natural fat and oil, are colorless, odorless and tasteless and further, exhibit little degradation with the lapse of time. They have, also, a wide range of from low viscosity to high viscosity and further, are lowered in a cloud point.

It should be, further, pointed out that the polar hydroxyl radical in the molecule not only plays an important role in the viscosity and solubility of the synthetic oil, but also serves to disperse even a synthetic oil of high viscosity into water and to wash out it easily with water and alcohols.

Table 1 shows properties of the synthetic oil of this invention together with controls.

Table 1

| Sample No. | Synthetic Oils | Color | Odor | Viscosity[1] Poise | Cloud[2] Point ° C |
|---|---|---|---|---|---|
| 1 | Di-2-octyldodecyl malate | Colorless and clear | Odorless | 1.18 | < −20 |
| 2 | Di-2-hexyldecyl tartrate | " | " | 5.4 | " |
| 3 | Di-2-heptylundecyl malate | " | " | 1.15 | " |
| 4 | 2-Octyldodecyl-5,7,7-trimethyl-2-(1,3,3-trimethyl-butyl)-octyl malate | " | " | 11.0 | " |
| 5 | Di-5,7,7,-trimethyl-2-(1,3,3-trimethyl-butyl)-octyl malate | " | " | 26.0 | " |
| 6 | Di-5,7,7,-trimethyl-2-(1,3,3-trimethyl-butyl)-octyl tartrate | " | " | 162.0 | " |
| 7 (Control) | Castor oil | Light yellow | Offensive odor | 6.1 | −10 ~ −13 |
| 8 (Control) | Dihexadecyl malate | | Solid, m.p. 51 ~ 54° C | | |

Note
[1] Measured at 25° C using Brookfield viscometer in accordance with Standard Method of Japan Oil Chemist's Society 2.3.9.5 — 71
[2] Measured in accordance with Standard Method of Japan Oil Chemist's Society 2.3.7 — 71

As is apparent from Table 1, all the compounds of this invention (Samples Nos. 1 to 6) are colorless, clear and odorless, whereas castor oil (Sample No. 7) shows light yellow and has peculiar odor. The compounds of this invention have a wide viscosity range including a relatively low viscosity, a viscosity of the castor oil grade and a remarkably high viscosity and are markedly low in the cloud point as compared with castor oil.

The control compound, dihexadecyl malate (Sample No. 8) of which alkyl has no side chain is a solid having a melting point of 51° - 54° C and therefore, can not be used for the purposes of this invention.

Next, the results of solubility tests of these compounds are given in Table 2.

Table 2

| Sample No. | (Measured at 25° C) | | |
|---|---|---|---|
| | Liquid Paraffin | Castor Oil | Ethanol |
| 1 | > 100% | > 100% | > 100% |
| 2 | " | " | " |
| 3 | " | " | " |
| 4 | " | " | " |
| 5 | " | " | " |
| 6 | " | " | " |
| 7 (Control) | 25% | > 100% | > 100% |
| 9 | > 100% | > 100% | 16% |

Table 2-continued

| Sample No. | (Measured at 25° C) | | |
|---|---|---|---|
| | Liquid Paraffin | Castor Oil | Ethanol |
| (Control)[3] | | | |

Note: Samples Nos. 1 – 7 are the same as the number in Table 1
[3] Di-(2-hexyl)-succinate It is apparent from Table 2 that the compounds of this invention (Samples Nos. 1 - 6) have good miscibility with various ingredients and therefore, are suitable for basic oils or emulsions. On the contrary, castor oil (Sample No. 7) is reduced in miscibility with liquid paraffin, while the control compound (Sample No. 9) which has no hydroxyl radical in the molecule is reduced in miscibility with ethanol.

Next, the primary irritant effect on the human body was evaluated by a closed patch test as follows: The horniness and sebum on the skin of the upper inner aspect of the arm were removed. The skin surface was covered with a cotton fabric of one inch square on which a sample was applied, and an oiled paper was covered thereon. Further, a paper adhesive plaster was covered in parallel crosses on the oiled paper and furthermore, a bandage was applied thereto. This test was effected on twenty men of health and rating was conducted after 24 hours, 48 hours and one week, respectively. None of the compounds of this invention (Samples Nos. 1 - 6) exhibited irritant effect on the skin. Thus, they have been found to be useful as a basic oil for cosmetics and medicinal preparations.

Further, odor tests were effected on twenty men of health by applying about 0.2 g of a sample within two inches around on the skin of the upper inner aspect of the arm and rating the odor after 10 minutes, 20 minutes, 30 minutes, one hour, 4 hours and 8 hours, respectively with olfactory sensation. None of the compounds of this invention (Samples Nos. 1 - 6) gave not an odor.

The compounds of the Formula I in which malic acid esters have one hydroxyl radical and tartaric acid esters two hydroxyl radicals are superior in the affinity and miscibility with water, humectants (or moisturizers) (for example, propylene glycol and glycerine) and surface active agents to the conventional basic oils which have no hydroxyl radical. Owing to the hydroxyl radical, they can be emulsified easily to a stable emulsion and have good oxidation resistance.

Among the compounds of the Formula I, esters of alcohols having a side chain in the β-position exhibit a good hydrolysis resistance, alkali resistance and acid resistance. The hydrolysis and acid resistance was determined according to the following method: About 2 g of a sample and 50 ml of a ⅓ N ethanol-hydrochloric acid (ethanol, 70%) were charged into a flask for measurement of saponification value, which was heated in a water bath at temperatures of 85° – 90° C for six hours. After cooling, a small amount of Bromophenol Blue indicator was added in dropwise and a titration was effected with a ½ N ethanol-potassium standard solution. A blank test was conducted at this time.

$$\text{Acid value} = \frac{28.05 \times (a - b) \times f}{c}$$

a: Amount of the ½ N ethanol-potassium standard solution required, ml.
b: Amount of the ½ N ethanol-potassium standard solution required in the blank test, ml.
c: Amount of the sample used.
f: Factor of the ½ N ethanol-potassium standard solution.

The measured acid values are given as follows:

| Samples | Acid Value |
| --- | --- |
| Castor Oil (Control) | 43.6 |
| Di-2-hexyldecyl tartrate | 15.9 |
| Di-5,7,7-trimethyl-2-(1,3,3-trimethylbutyl)-octyl malate | 12.9 |
| Di-2-octyldodecyl malate | 14.2 |

The foregoing show that the synthetic oils of this invention are superior in the acid resistance to the natural castor oil.

Owing to such properties, the oxyacid esters of this invention are useful as basic oils for soaps, rinse and the like.

This invention is illustrated by the following non-limitative examples.

EXAMPLE 1

To a four-necked flask of a 2l capacity provided with a stirrer, a thermometer, a nitrogen gas blowing tube and a water separating apparatus, 1.58 mols of tartaric acid, 3.0 mols of 2-hexyl decanol and 20% by weight of toluene based on the total charge were added while stirring and then, p-toluenesulfonic acid as an esterification catalyst was added.

Reaction was effected at 120° to 130° C till a calculated amount of water had been collected in the water separating apparatus. The time required was about 4 hours. After completion of reaction, the obtained product was subject to deacidification in the conventional methods and then to decoloration with use of a decoloring agent of an activated clay - active carbon type, followed by deodorizing under reduced pressure with steam stripping. Thus obtained end product, di-2-hexyldecyl tartrate is colorless, odorless and tasteless. Yield: 86%, Acid value: 0.30, Hydroxyl value: 182.3 (Calculated value 187.3), Saponification value: 181.9 (Calculated value 187.3), Viscosity: 5.4 poises at 25° C

EXAMPLE 1—1

A lipstick was prepared using the following formulation containing the oxyacid ester of Example 1 as a basic oil.

| Ingredients | % by weight |
| --- | --- |
| Bees wax | 18 |
| Carnauba wax | 8 |
| Di-2-hexyldecyl tartrate | 60 |
| Lanolin | 5 |
| Hardened oil | 3 |
| Dyestuff solution | 2 |
| Perfumes | 2 |
| Pigments | 2 |

The above oil and fat materials were melted with heating, the pigments were dispersed therein, and the dyestuff solution was added while stirring, then the perfumes was added. The obtained product was formed to a lipstick while stirring gently. This lipstick has no offensive taste and a good feeling without stickiness.

EXAMPLE 2

Reaction of 1.37 mols of malic acid with 2.66 mols of 5,7,7-trimethyl-2-(1,3,3-trimethylbutyl)-octanol-1, the subsequent deacidification, decoloration and deodorizing were effected in the same procedure as in Example 1.

Thus obtained end product, di-5,7,7-trimethyl-2-(1,3,3-trimethylbutyl)-octyl malate is colorless, odorless and tasteless. Yield: 88%, Acid value: 0.20, Hydroxyl value: 86.2 (Calculated value 87.3), Saponification value: 176.2 (Calculated value 174.6), Viscosity: 26.0 poises at 25° C 5,7,7-Trimethyl-2-(1,3,3-trimethylbutyl)-octanol-1 used as the starting material is sold under the tradename, Fineoxocol 180 by Nissan Chemistry Co., Japan.

EXAMPLE 2—1

A hair tonic was prepared using the following formulation containing the oxyacid ester of Example 2 as a basic oil.

| Ingredients | % by weight |
| --- | --- |
| Ethanol | 85.0 |
| Di-5,7,7-trimethyl-2-(1,3,3-trimethylbutyl)-octyl malate | 14.7 |
| Salicylic acid | 0.3 |
| Perfumes | Small amounts |
| Dyestuffs | Small amounts |

The above materials and additives were added to ethanol and dissolved sufficiently, then added with the perfumes and dyestuffs while stirring, and after filtration, poured into a container.

The thus obtained hair tonic, because of the basic oil being used in reduced amount as compared with the conventional hair tonic, has no stickiness and also a good hairdressing effect. This hair tonic has no irritant effect and a good stability at low temperature, and further does not interrupt the metabolism of the skin because of the steam permeability being moderate.

EXAMPLE 3

Reaction of 1.23 mols of malic acid with 2.4 mols of 2-octyl dodecanol, the subsequent deacidification, decoloration and deodorizing were effected in the same procedure as in Example 1.

Thus obtained end product, di-2-octyldodecyl malate is colorless, odorless and tasteless. Yield: 95%, Acid value: 0.05, Hydroxyl value: 82.0 (Calculated value 79.9), Saponification value: 147.2 (Calculated value 159.8), Viscosity: 1.18 poises at 25° C.

2-octyl dodecanol used as the starting material is sold under the tradename, NJ Col-200A by Shin Nihon Rika Co., Japan.

EXAMPLE 3—1

Liquid cream was prepared using the following formulation containing the oxyacid ester of Example 3 as a basic oil.

| Ingredients | % by weight |
| --- | --- |
| Bees wax | 16.0 % |
| Liquid paraffin | 20.0 % |
| Di-2-octyldodecyl malate | 30.5 % |
| Distilled water | 32.0 % |
| Sodium borate | 1.0 % |
| Perfumes | 0.5 % |
| Antioxidants | Small amounts |
| Preservatives | Small amounts |

The above oil and fat materials, perfumes, antioxidants and perservatives were mixed together with, melted and maintained at 70° C, while sodium borate was dissolved in the distilled water and heated at 70° C. These two components were mixed at 70° C, emulsified and cooled to 30° C while stirring.

The obtained product is a liquid cream having a good smoothness and spread.

EXAMPLE 4

A cream rinse was prepared using the following formulation containing the oxyacid ester of Example 3 as a basic oil. Formulation:

| | | % by weight |
| --- | --- | --- |
| Mixture A | Diethyleneglycol monostearate | 5.0 |
| | Distearyl-dimethyl ammonium chloride | 3.0 |
| | Di-2-octyldodecyl malate | 4.0 |
| | Lanolin | 2.0 |
| | Methylparaben | 0.1 |
| | Ethylparaben 0.1 | |
| Mixture B | Proplene glycol | 3.0 |
| | Citric acid | 0.2 |
| | Sodium citrate | 0.15 |
| | Distilled water | 82.55 |
| Component C | Perfumes | Small amounts |

The mixture A was heated at 80° C and dissolved well while stirring, and the mixture B heated at 80° C was added thereto and emulsified. The obtained emulsion was cooled while stirring, added with the perfumes (Component C) at 50° C, then cooled to 35° C, and after defoaming, poured into a container.

Thus obtained cream rinse makes the hair flexible and glossy.

EXAMPLE 5

2 mols of tartaric acid, 4.1 mols of 2-heptyl undecanol and 0.2% by weight of para-toluenesulfonic acid based on the total charge were charged into a four-necked flask of a 2l capacity. After reaction at a temperature of 100° – 120° C under a reduced pressure of 5 – 100 mmHg, the subsequent deacidification, decoloration and deodorizing were effected in the same procedure as in Example 1.

Thus obtained end product, di-2-heptylundecyl tartrate is colorless, odorless and tastless. Yield: 82%, Acid value: 0.05, Hydroxyl value: 167 (Calculated value 168.7), Saponification value: 160 (Calculated value 168.7), Viscosity: 267 cps at 25° C 2-Heptyl undecanol used as the starting material is sold under the tradename, Diadol 18G by Mitsubishi Kasei Co., Japan. This Diadol 18G contains 19% of 2-heptyl-4-methyl decanol-1 and 1% of other isomers.

EXAMPLE 5—1

A solid soap was prepared using the following formulation containing the oxyacid ester of Example 5 as a basic oil.

| Ingredients | % by weight |
| --- | --- |
| Sodium stearyl sulfonate | 30.0 |
| Coconut oil soap | 55.0 |
| Di-2-heptylundecyl tartrate | 5.0 |
| Builders | 10.0 |
| Dyestuffs and Perfume | Small amounts |

The ingredients other than the dyestuff and perfume were kneaded well while heating, then cooled and added with the dyestuff and perfume.

The above oxyacid ester is effected as a superfatting agent for the soap.

EXAMPLE 6

2 mols of malic acid, 4.20 mols of 2-heptyl undecanol and 0.5% by weight of zinc acetate based on the total charge were added into a four-necked flask of a 2l capacity, and the reaction and subsequent decoloration and deodorizing were effected in the same procedure as in Example 1.

Thus obtained end product, di-2-heptylundecyl malate is substantially colorless and odorless. Yield: 84%, Acid value: 0.30, Hydroxyl value: 80.1, Saponification value: 169, Viscosity: 1.15 poises at 25° C

EXAMPLE 7

2 mols of tartaric acid, 4.10 mols of 5,7,7-trimethyl-2-(1,3,3-trimethylbutyl)-octanol-1 and 0.2% by weight of stannous chloride based on the total charge were added into a four-necked flask of a 2l capacity. After reaction at a temperature of 120° C under a reduced pressure of 10 – 100 mmHg, the decoloration and deodorizing were effected in the same procedure as in Example 1.

Thus obtained end product, di-5,7,7-trimethyl-2-(1,3,3-trimethylbutyl)-octyl tartrate is substantially colorless and odorless.

Yield: 86%, Acid value: 0.10, Hydroxyl value: 170, Saponification value: 167, Viscosity: 162 ps. at 25° C

What is claimed is:

1. Hydroxy diester compounds represented by the Formula I,

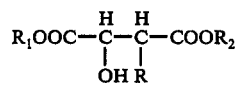

wherein R is hydrogen or hydroxyl, and $R_1$ and $R_2$ which may be the same or different are selected from the group consisting of 2-hexyldecyl, 2-octyldodecyl, 2-heptylundecyl or 5,7,7-trimethyl-2-(1,3,3-trimethylbutyl)-octyl.

2. Di-2-hexyldecyl tartrate.

3. Di-5,7,7-trimethyl-2-(1,3,3-trimethylbutyl)-octyl malate.

4. Di-2-octyldodecyl malate.

5. Di-2-heptylundecyl tartrate.

6. Di-2-heptylundecyl malate.

7. 2-octyldodecyl-5,7,7-trimethyl-2-(1,3,3-trimethylbutyl)-octyl malate.

8. Di-5,7,7-trimethyl-2-(1,3,3-trimethylbutyl)-octyl tartrate.

9. Basic oils comprising the hydroxyl diester compounds of Formula I as an essential ingredient

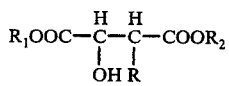

wherein R is hydrogen or hydroxyl, and $R_1$ and $R_2$ which may be the same or different, are a member selected from the group consisting of 2-hexyldecyl, 2-octyldodecyl, 2-heptylundecyl or 5,7,7-trimethyl-2-(1,3,3-trimethylbutyl)-octyl.

10. Emulsions comprising the hydroxy diester compounds of Formula I as an essential ingredient

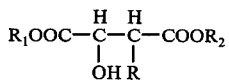

wherein R is hydrogen or hydroxyl, and $R_1$ and $R_2$ which may be the same or different, are a member selected from the group consisting of 2-hexyldecyl, 2-octyldodecyl, 2-heptylundecyl or 5,7,7-trimethyl-2-(1,3,3-trimethylbutyl)-octyl.

11. Cosmetics comprising the hydroxy diester compounds of Formula I as an essential basic oil

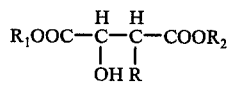

wherein R is hydrogen or hydroxyl, and $R_1$ and $R_2$ which may be the same or different, are a member selected from the group consisting of 2-hexyldecyl, 2-octyldodecyl, 2-heptylundecyl or 5,7,7-trimethyl-2-(1,3,3-trimethylbutyl)-octyl.

12. Medicinal preparations comprising the hydroxy diester compounds of Formula I as an essential basic oil

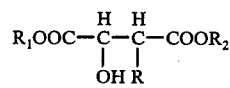

wherein R is hydrogen or hydroxyl, and $R_1$ and $R_2$ which may be the same or different, are a member selected from the group consisting of 2-hexyldecyl, 2-octyldodecyl, 2-heptylundecyl or 5,7,7-trimethyl-2-(1,3,3-trimethylbutyl)-octyl.

13. Soaps comprising the hydroxy diester compounds of Formula I as an essential basic oil

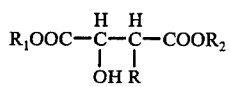

wherein R is hydrogen or hydroxyl, and $R_1$ and $R_2$ which may be the same or different, are a member selected from the group consisting of 2-hexyldecyl, 2-octyldodecyl, 2-heptylundecyl or 5,7,7-trimethyl-2-(1,3,3-trimethylbutyl)-octyl.

14. The emulsion of claim 10, which is a cosmetic.

15. The emulsion of claim 10, which is a medicinal preparation.

16. The emulsion of claim 10, which is a soap.

17. The emulsion of claim 10, which is a rinse.

18. The medicinal preparation of claim 12, which is an ointment.

19. The medicinal preparation of claim 12, which is an emulsion.

20. Rinses comprising the hydroxy diester compounds of Formula I as an essential basic oil

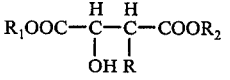

wherein R is hydrogen or hydroxyl, and $R_1$ and $R_2$ which may be the same or different, are a member selected from the group consisting of 2-hexyldecyl, 2-octyldodecyl, 2-heptylundecyl or 5,7,7-trimethyl-2-(1,3,3-trimethylbutyl)-octyl.

* * * * *